July 18, 1950 E. MULLER Plant Pat. 965
DOGWOOD PLANT
Filed Aug. 1, 1949
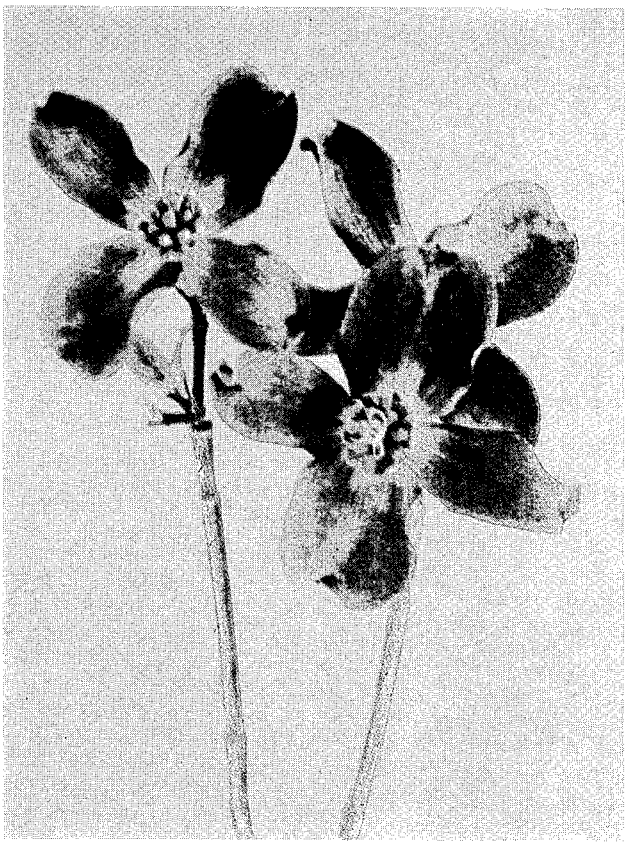
Inventor
E. Muller
By Robbins & Robb
attorneys Patented July 18, 1950

Plant Pat. 965

UNITED STATES PATENT OFFICE

965

DOGWOOD PLANT

Eugene Muller, Norristown, Pa.

Application August 1, 1949, Serial No. 107,983

1 Claim. (Cl. 47—59)

The present discovery relates to a new and distinct variety of dogwood tree, originating as a sport of the Pink Dogwood, generally known as *Cornus florida* rubra.

This new variety differs rather extensively from its parent in habits of growth, texture or appearance of its foliage, and more importantly, color of the flowers as will now be set forth in detail.

While the shape of the tree is about the same as the free growing common Pink Dogwood variety, this mutation is definitely very much smaller to the extent that it may be said to be dwarf, or perhaps semi-dwarf. That is to say, comparison of the trees in the nurseries, shows the new variety to be about one-half the size of other Pink Dogwood, planted at the same time and grafted at the same time. The new dogwoods are approximately three to three and a half feet high, while the Pink Dogwoods which were planted alongside in exactly the same soil and treated in exactly the same manner are six to seven feet high.

The foliage of the new variety is a much deeper green color than that of the parent variety and further the leaves turn to a considerably deeper color of red in the fall than do the normal Pink Dogwoods. While in size and shape the leaves of the new variety are similar to those of the Pink, their texture or appearance is entirely different in that they are wavy or rough.

This new variety tree is a sturdy, healthy grower and a rather free bloomer. The flowers are completely different in color from those of the Pink Dogwoods, being of a deep, rich, heavy wine-red color, instead of light pink. This is the most significant characteristic of this new variety.

Asexual reproduction of this new variety shows that the foregoing characteristics come true to form and are established.

In the drawing are illustrated specimens of the flowers clearly depicting their color and form.

This new variety was asexually reproduced at Norristown, Montgomery County, Pennsylvania, by grafting.

The following is a detailed description of the new variety, based upon observations of specimens grown at Norristown, Montgomery County, Pennsylvania, color terminology being in accordance with Ridgway's Color Standards and Nomenclature, except where indicated to have ordinary dictionary significance:

*Tree*

Small; medium vigorous; upright; dense; round-topped; hardy; very productive; regular bearer.

Trunk: stocky; smooth.

Branches: Stocky; smooth; brown; dull. Lenticels—numerous.

Leaves: Length—about 2½''; width—about 1½''. Oval; acuminate; medium thick; medium light green color; rugose.

*Margin.*—Crenate; rounded edge; slightly wavy.

*Petal-like bracts.*—Range from Pomegranate Purple to Bordeaux when flower is old, Plate XII.

*Tip of bracts.*—Blends into a Slate-Gray, Plate LIII.

*Small new leaves.*—Grayish-Lavender, Plate XLIII, with veins of Daphne Pink, Plate XXXVIII.

*Stems.*—Blackish Brown (3), Plate XLV. Bloom on stems—Pale Mouse Gray, Plate LI.

*Glands (or veins of total leaf area).*—Average number—about 10 or 12, depending on size of leaves. Opposite; medium size; globose; green.

*Stipules at base of small leaf stem.*—Hessian Brown, Plate XIII.

Flower buds: Hardy; medium size; medium length; plump; free; smooth.

Flowers:

*Dates first and full bloom.*—Approximately April 15th–April 20th. Medium early compared with other varieties.

*Size.*—Medium.

*Color.*—Wine Red.

*Small flowers when open.*—Light Viridine Yellow, Plate V. Tips—Garnet Brown, Plate I.

*Anthers (with the pollen).*—Empire Yellow, Plate IV.

*Pistil.*—Pale Viridine Yellow, Plate V.

I claim:

A new and distinct variety of dogwood tree, characterized as to novelty by its dwarfish habit of growth, by the texture of the leaves and their dark green color turning in the fall to dark red color, and by the deep, rich, heavy wine-red color of the flowers, substantially as shown and described.

EUGENE MULLER.

No references cited.